United States Patent [19]

Long

[11] Patent Number: 4,993,415

[45] Date of Patent: Feb. 19, 1991

[54] MAGNETIC RESONANCE IMAGING WITH PERFLUOROCARBON HYDRIDES

[75] Inventor: David M. Long, El Cajon, Calif.

[73] Assignee: Alliance Pharmaceutical Corp., Otisville, N.Y.

[21] Appl. No.: 551,884

[22] Filed: Jul. 12, 1990

Related U.S. Application Data

[62] Division of Ser. No. 234,193, Aug. 19, 1988, Pat. No. 4,951,673.

[51] Int. Cl.$^5$ .............................................. A61L 15/00
[52] U.S. Cl. .................................. 128/653 A; 514/761; 424/5
[58] Field of Search .................... 128/653, 654, 659; 424/1.1, 4, 9, 5; 514/757, 761; 436/173

[56] References Cited

U.S. PATENT DOCUMENTS

| | | | |
|---|---|---|---|
| 3,818,229 | 6/1974 | Long | . |
| 3,975,512 | 8/1976 | Long | 514/761 |
| 4,073,879 | 2/1978 | Long | 514/761 |
| 4,215,103 | 7/1980 | Millington | 424/4 |
| 4,448,188 | 5/1984 | Leob | 128/303.1 |
| 4,586,511 | 5/1986 | Clark, Jr. | 128/653 A |
| 4,612,185 | 9/1986 | Dean | 424/4 |
| 4,640,833 | 2/1987 | Tamborski | 424/5 |
| 4,742,050 | 5/1988 | Yuhas et al. | 514/34 |
| 4,767,610 | 8/1988 | Long | 424/5 |
| 4,781,676 | 11/1988 | Schwweighardt | 600/1 |
| 4,815,446 | 3/1989 | McIntosh | 600/3 |

FOREIGN PATENT DOCUMENTS

| | | | |
|---|---|---|---|
| 0188281 | 9/1984 | European Pat. Off. | . |
| 2099579 | 12/1982 | United Kingdom | 436/173 |

OTHER PUBLICATIONS

Longmaid III et al., "In Vivo 19F NMR Imaging", Investigative Radiology, Mar.-Apr. 1985, vol. 20, pp. 141-145.

Mattrey, "Perfluorocarbon Compounds; Applications in Diagnostic Imaging", SPIE, vol. 626, Medicine XIV/PACS IV (1986), pp. 18-23.

Patronas et al., "Brain-Tumor Imaging Using Radiopaque Perfluorocarbon", J. Neurosurg., vol. 58, May 1983, pp. 650-653.

Thomas et al., "NMR Imaging of the Lung Using Liquid Perfluorocarbon", pp. 717-718, J of Comput. Assist. Tomogr., Jan.-Feb. 1986, vol. 10, No. 1, pp. 1-9.

Freeman et al., "Rapid $^{19}$FMR Imaging of PFOB in Vivo", Magnetic Resonance Imaging, vol. 6, pp. 61-64, 1988.

Joseph et al., "In Vivo $^{19}$F NMR Imaging of the Cardiovascular System", J. of Computer Assisted Tomography, vol. 9, No. 6, 1985, pp. 1012-1019.

Hishikawa et al., "Tumor Imaging with Conventional X-Ray Using a New Artificial Blood Substitute PFOB Emulsion", Gan to Kagakui Ryoho, vol. 11, No. 10, 1984, pp. 2236-2244.

Long et al., "Preparation and Applications of Highly Conc. PFOB Emulsions", 3rd International Symposium on Blood Substitutes, Montreal, Quebec, Canada, May 26-28, 1987.

Horner et al., "Evaluation of Myocardial Perfusion by $^{19}$NMR Imaging", pp. 338-339.

Sartoris et al., "Perfluoroctylbromide as a Contrast Agent for CT Imaging of Septic and Aseptic Arthritis", Invest. Radiol., vol. 21, No. 1, 1986, 49-55, 1986.

Young et al., "Perfluoroctylbromide Contrast Enhancement of Malignant Neoplasms", Am J. Roentgenol; 137, pp. 141-146, Jul. 1981.

Joseph et al., "MR Imaging of Fluorine in Bata Infused with Antificial Blood", Invest. Radiology, vol. 20, No. 5, pp. 504-509, Aug. 1985.

Koutcher et al., "In Vivo Imaging and Spectroscopy of Fluorinated Blood Substitutes", J. of Comput. Assist. Tomogr., Jan.-Feb. 1985, vol. 9, No. 1, pp. 8-15.

Horner et al., "Evaluation of Myocardial Perfusion by $^{19}$F NMR Imaging", Magn. Reson. Imaging, vol. 3, Iss. 4, pp. 399-405, 1985.

Newhouse, J. R. et al., "NMR Scanning of the Abdomen: Preliminary Results in Small Animals", NMR Imaging 121-124, The Bowman Gray School of Medicine of Wake Forest University, Winston-Salem, N.C. (1982).

Bydder, G. M., "Clinical NMR Results from Second Nuclear Magnetic Imaging Symposium", Winston-Salem: 1981.

(List continued on next page.)

Primary Examiner—C. Fred Rosenbaum
Assistant Examiner—Sharon Rose
Attorney, Agent, or Firm—Knobbe, Martens, Olson & Bear

[57] ABSTRACT

Perfluorocarbon hydrides, either alone or in combination with other perfluorocarbon compounds, may be introduced into a non-vascular animal space as a contrast agent in magnetic resonance imaging (MRI), computed tomography (CT) or conventional x-ray procedures. In the image generated by these systems, the fluorocarbon introduced into the space is contrasted with the remaining body tissues or spaces to distinguish the fluorocarbon-occupied space from other tissues and spaces.

Perfluoroctyl hydride vaporizes at body temperature, and its gas phase, which also provides in effective contrast to tissues, is disclosed in imaging areas of comparatively large void volume while using a lower fluorocarbon dose then than required for fluid fluorocarbon.

Perfluorocarbon hydrides offer less radiodensity to x-ray imaging and less hydrogen density to MRI imaging, and are disclosed as diluents for perfluorocarbon bromides in applications where concentrated brominated compounds are found to cause imaging artifacts.

Perfluorocarbon emulsions comprising a mixture of perfluorocarbon bromide and at least 0.1% perfluorocarbon hydride are disclosed for intravascular use as a contrast agent or for oxygen transport.

7 Claims, No Drawings

OTHER PUBLICATIONS

Young, I. R. et al., "Initial Clinical Evaluation of Whole Body NMR Tomograph", J. of Computer Assisted Tomography, 6:1-18 (1982).

Geyer, R., "Perfluorocarbon Blood Substitutes", International Symposium on Artificial Blood Substitutes, Bari, Italy: Jun. 19-20 (1987).

Long, D. C. et al., "Preparation and Application of Highly Concentrated PFOB Emulsions", Biomat., Art. Cells, Art. Organs, 15(2), 417 (1987).

Long, D. M. et al., "Overview of Experimental and Clinical Applications of PFOB", Biomat., Art. Cells, Art. Organs, 15(2), 418 (1987).

Mattrey, R. F., "Perfluorochemicals as US Contrast Agents for Tumor Imaging and Hepatosplenography", Radiology, 163:339-343 (1987).

"Ultrasound Enhancement of Tissues During the Capillary Phase of PFOB-100% Immediately Post Infusion", 35th Annual Meeting of the Association of University Radiologists, Charleston, S. C.: Mar. 22-27 (1987).

Mattrey, R. F., "IV Contrast: Using it to Optimize CT Diagnosis", Advances in Sectional Imaging, pp. 105-106, San Diego: Sep. 10-12, 1987.

Longmaid, H. E. et al., "In Vivo $^{19}$F Imaging of Liver, Tumor and Abscess in Rats", Investigative Radiology 20:141-145 (1985).

Mattrey, R. F. et al., "Preliminary Clinical Results Using Perfluoroctylbromide as an MR Imaging Gastrointestinal Contrast Agent for Proton Imaging", Radiology 161:P, p. 314 (1986).

Dobben, G. et al., "Experimental Studies with Radiopaque Fluorocarbon in the Subarachnoid Space", Neuroradiology 6:17-19 (1973).

Brahme, F. et al., "Perfluorocarbon Bromides as Contrast Media in Radiography of the Central Nervous System", Acta Red., Sup. 347:459-466 (1975).

Liu, M. S. et al., "Myelography with Perfluoroctylbromide: Comparison with Pantopaque", Investigative Radiology 11(4):319-330 (1976).

Burgan, A. et al., "Acute and Subacute Toxicity of 100% PFOB Emulsion", 5th Annual Meet., Soc. of Magnet. Resonance in Med., Montreal: Aug. 18-22 (1986).

Long, D. et al., "Total Exchange Perfusion of Rats with Highly Concentrated Fluorocarbon Emulsions", International Symposium, Centenary of the Discovery of Fluorine, Paris: Aug. 25-29 (1986).

Arlen, C. et al., "Formulation of Highly Concentrated Fluorocarbon Emulsions and Assessment by Near-Total Exchange Perfusion of the Conscious Rat", Biomat. Art. Cells, Art. Organs, 15(2), 431 (1987).

Mattrey, R. F. et al., "Perfluorocarbons as Gastrointestinal Contrast Agents for MR Imaging: Preliminary Studies in Rats and Humans", Amer. J. of Radiology 148: 1259-1263 (1987).

Mattrey, R. R. et al., "Perfluorohexylbromide as an MRI Gastrointestinal Contrast Agent for Proton Imaging", 5th Annual Meeting of the Society of Magnetic Resonance Imaging in Medicine, Montreal: Aug. 18-22 (1986).

Menghetti, R. et al., "Evaluation of Fluorochemical Distribution After Ventricular Injection as Determined by Computer Assisted Tomography" (1987).

MAGNETIC RESONANCE IMAGING WITH PERFLUOROCARBON HYDRIDES

This application is a division of application Ser. No. 234,193, filed Aug. 19, 1988, now U.S. Pat. No. 4,951,673.

BACKGROUND OF THE INVENTION

The present invention relates to radiological imaging systems, and more particularly to use of a contrast enhancing agent in imaging parts of an animal body according to methods of magnetic resonance imaging (MRI), computed tomography (CT), or conventional radiography (X-ray).

Contrast agents are useful adjuncts in radiological imaging procedures because they make it possible to determine the location, size and conformation of organs or other structures of the body in the context of their surrounding tissues.

Cells which make up the tissues of soft non-bony body parts are comprised primarily of water even among parts that differ markedly in shape and structure such as the liver, pancreas and intestine. Radiography procedures of computed tomography and magnetic resonance imaging operate on the basis of distinct physical principles, but each detects and maps differences in the composition of a target object; therefore these procedures often fail to provide satisfactory images of contiguous body parts without the aid of a contrast agent. In the diagnosis of disorders of the digestive tract, for example, blockage or abnormalities in the conformation of loops of intestine lying one on the other are difficult to identify unless the section of the gastrointestinal tract is filled with a contrast agent to define volumes and delineate boundaries.

In the conventional radiographic procedure, a beam of x-rays passes through a target object and exposes an underlying photographic film. The developed film then provides a image of the radiodensity pattern of the object. Less radiodense areas produce a greater blackening of the film; more radiodense, bony tissues produce a light image. Effective contrast agents for x-ray may be either less radiodense than body tissues or may be more radiodense. The less radiodense agents comprise air or another gas. For example, a patient may be assisted to swallow air in order to better visualize the upper gastrointestinal tract, or air may be introduced into the ventricles of the brain in procedures to visualize these structures. An example of a more radiodense contrast material is a barium sulfate suspension which is commonly introduced into the bowel prior to radiographic imaging.

Computed tomography (CT) is superior to conventional radiography in its ability to image a succession of thin sections of an object at specific points, lines or planes along the X, Y or Z axis of the target object and to do this with extremely high resolution; but because this procedure is also based on the detection of differences in radiodensity, requirements for contrast agents in computed tomography are identical with those for conventional radiography.

Nuclear magnetic resonance imaging (MRI) systems for body imaging operate on a different physical principle. Literature describing the theoretical and practical use of MRI systems are available from manufacturers such as the General Electric & Co. who market commercial systems. A general reference on the background and theoretical description of the MRI system, the publication entitled "NMR Tomography" by William G. Bradley (1982), is available from Diasonics, Inc., Milpitas, Calif., and is attached hereto as an appendix and incorporated herein for convenience.

In the magnetic resonance imaging systems, advantage is taken of the fact that some atomic nuclei, such as, for example, hydrogen nuclei, have both nuclear spin and nuclear magnetic moment, and therefore can be manipulated by applied magnetic fields. In the customary type of MRI system, a magnetic field is established across a body to align the spin axes of the nuclei of a particular chemical element, usually hydrogen, with the direction of the magnetic field. The aligned, spinning nuclei execute precessional motions around the aligning direction of the magnetic field. For the aligned, spinning nuclei, the frequency at which they precess around the direction of the magnetic field is a function of the particular nucleus which is involved and the magnetic field strength. The selectivity of this precessional frequency with respect to the strength of the applied magnetic field is very sharp and this precessional frequency is considered a resonant frequency.

In a customary MRI system, after alignment or polarization of the selected nuclei, a burst of radio frequency energy at the resonant frequency is radiated at the target body to produce a coherent deflection of the spin alignment of the selected nuclei. When the deflecting radio energy is terminated, the deflected or disturbed spin axes are reoriented or realigned, and in this process radiate a characteristic radio frequency signal which can be detected by an external coil and then discriminated in the MRI system to establish image contrast between different types of tissues in the body. MRI systems have a variety of different excitation and discrimination modes available, such as, for example, free induction decay ("FID"), spin echo, continuous wave, which are known in the art.

Two parameters are used to measure the response of the magnetized sample to a disturbance of its magnetic environment. One is $T_1$ or "thermal" relaxation time, the time it takes the sample to become magnetized or polarized after being placed in a external magnetic field; the other is $T_2$, the spin-spin relaxation time, a measure of the time the sample holds a temporary transverse magnetization which is perpendicular to the external magnetic field. Images based on proton density can be modified by these two additional parameters to enhance differences between tissues.

Hydrogen has been usually selected as the basis for MRI scanning because of its abundance in the water content of the body and its prominent magnetic qualities. It is believed that investigations are being conducted to determine if sodium and phosphorous would also be satisfactory as the basis for magnetic resonance imaging.

Contrast agents for MRI must posses a substantially different concentration of the nuclei used as a basis for scanning. In a hydrogen scanning system, an agent substantially lacking hydrogen can be used; in an MRI system which scans for a physiologically minor nucleus, for example, the fluorine nuclei, a substance with a high concentration of that nucleus would provide appropriate contrast.

Contrast agents may be introduced into the body space in various ways depending on the imaging requirement. In the form of liquid suspensions or emulsions they may be placed in the gastrointestinal tract by oral ingestion or by rectum, inserted into bodily spaces like the peritoneal cavity or injected into the vascular system either generally or into the vessels of a specific organ such as the coronary artery.

A suitable contrast agent must be biocompatible, that is non-toxic and chemically stable, not absorbed by the body or reactive with the tissue, and eliminated from the body within a short time. Few satisfactory agents have been developed for MRI. Imaging of the gastrointestinal tract of animals has been enhanced with large doses of mineral oil. (Newhouse, JR, et al: Abdominal NMR Imaging: Normal Anatomy, Fluid Collections and a New Contrast Agent, presented at 67th Scientific Assembly of RSNA, Chicago, Ill., Nov. 15-20, 1981). Magnesium cations have been used in the study of experimental myocardial infarction, (Rydder GM: Clinical NMR Results from Second Nuclear Magnetic Imaging Symposium. Winston-Salem, N.C., 1981 (in press)). Inhaled oxygen can also provide contrast in the heart (Young IR, et al., Initial Clinical Evaluation of Whole Body NMR Tomograph. J. of Comput. Assist. Tomograph. 6:1-18. February 1982).

It is known to use perfluorocarbons, including brominated perfluorocarbons, as a contrast enhancement medium in radiological imaging as shown in U.S. Pat. No. 3,975,512 to Long, the applicant herein. Brominated and other fluorocarbons are known to be safe and biocompatible when used internally in the body. It is also known to use these agents in the context of the MRI procedure to contrast more clearly and more distinctly in MRI-produced images the several body parts which normally have substantially higher water content and which are close or overlaid one on the other.

It is desirable to provide other compounds of this class which can be used even more safely, more efficiently, and more economically. It is therefore an object of the invention to provide contrast agents which are even less readily absorbed by the body and operate in such a manner as to reduce the total amount of material necessary to provide a satisfactory radiological or magnetic resonance image.

BRIEF SUMMARY OF THE INVENTION

In accordance with the object of the invention, there is provided a method for using imaging compositions comprising perfluorocarbon hydrides as contrast agents when these hydrides are introduced into the non-vascular spaces of the body. The lipophobic character of these compounds reduces the possibility that they will be absorbed into the body tissues, and their ability to vaporize at body temperatures provides advantages in specific imaging applications.

According to one aspect of the invention there is provided a method for imaging a selected non-vascular space of an animal body using magnetic resonance imaging by introducing an imaging composition comprising a perfluorocarbon hydride having from six to ten carbon atoms into the non-vascular body space to at least partially fill the space and then imaging the space and surrounding tissues with a magnetic resonance proton imaging system to contrast the fluorocarbon-occupied space with a surrounding space or tissue which contains substantially greater concentrations of protons. In one embodiment the imaging composition is introduced into the animal body orally prior to the imaging step. In a preferred embodiment, the perfluorocarbon hydride comprises perfluoroctyl hydride.

In another embodiment of the invention the imaging composition further comprises a perfluorocarbon bromide. In a preferred embodiment, the imaging composition comprises perfluoroctyl bromide in combination with perfluoroctyl hydride.

In yet another embodiment of the invention, the method further comprises the step prior the imaging step of allowing the imaging composition to at least partially vaporize in situ within the body space into which is has been introduced. In a preferred embodiment, the body space into which the imaging composition is permitted to vaporize is the bowel. Alternatively, the body space into which the imaging composition is allowed to vaporize is the peritoneal space.

In accordance with another aspect of the invention, there is provided a method for imaging a selected non-vascular space of an animal body by computed tomography, comprising introducing a fluorocarbon mixture comprising a perfluorocarbon bromide having from six to ten carbon atoms and a perfluorocarbon hydride having from six to ten carbon atoms into the non-vascular body space to at least partially fill the space and then imaging the space and its surrounding tissues with a computed tomography system to contrast the fluorocarbon-occupied space with a surrounding space or tissues containing substantial concentrations of less radiodense material.

In one embodiment said perfluorocarbon mixture is introduced into the animal body orally before computed tomography imaging. In a preferred embodiment, the perfluorocarbon hydride of the perfluorocarbon mixture is at least partially vaporized in situ within the body space. The body space may comprise the bowel of said animal or alternatively may comprise the peritoneal cavity.

In accordance with yet another aspect of the invention there is provided a method for imaging a selected nonvascular body space of an animal body comprising introducing an imaging composition comprising a perfluorocarbon hydride having from six to ten carbons atoms into the non-vascular body space to at least partially fill the space and then imaging the space and surrounding tissues by conventional X-radiography to contrast the fluorocarbon-occupied space with the surrounding space or tissue which contains substantial concentrations of less radiodense material.

In one embodiment of this aspect of the invention the imaging composition of the radiographic method comprises perfluoroctyl bromide in combination with perfluoroctyl hydride. In another embodiment, the introducing step of the method may comprise oral introduction of the imaging composition. In a preferred embodiment, the method further comprises the step, before the imaging step, of permitting the imaging composition to at least partially vaporize in situ within said body space. The body space may, for example, be the bowel of the animal, or alternatively the peritoneal space.

In any of the above embodiments of the method, the imaging composition may further comprise perfluorohexyl bromide. In a specific embodiment the perfluorocarbon compounds of said imaging composition are in the form of an emulsion further comprising an emulsifying agent and a physiologically acceptable aqueous phase.

According to yet another aspect of the invention, there is provided a fluorocarbon emulsion for use in an animal body, comprising a physiologically acceptable aqueous phase; a perfluorocarbon mixture comprising a perfluorocarbon bromide and at least 0.1% of a perfluorocarbon hydride having from six to ten carbon atoms said perfluorocarbon mixture at a concentration of 20% to 125% weight per volume in said emulsion; and an effective amount of an emulsifying agent. Alternatively, the emulsion comprises an effective oxygen carrying amount of said perfluorocarbon mixture. In preferred embodiments, the perfluorocarbon bromide is perfluoroctyl bromide and the perfluorocarbon hydride is perfluoroctyl hydride. In a particularly preferred embodiment, the emulsifying agent is a phosphlipid.

There is further provided a method for imaging a selected tissue of an animal body comprising introducing a fluorocarbon emulsion comprising perfluorocarbon hydride into the vascular system of the body. There is further provided a method for carrying oxygen to the tissues of an animal body comprising introducing an oxygen-carrying emulsion comprising perfluorocarbon hydride into the vascular system of the body.

These and other advantages and features of the present invention will become more fully apparent from the following description and appended claims.

DETAILED DESCRIPTION OF THE PREFERRED EMBODIMENT

Perfluorocarbon hydrides, either alone or in combination with similar compounds, are effective contrast agents for use in medical diagnostic imaging procedures.

The physical homogeneity of the non-bony tissues makes it difficult to define the contours and limits of the various organs and structures, whether the basis of imaging is proton spin, as in magnetic resonance imaging (MRI) or radiodensity, as in conventional radiography (x-ray) and computed tomography (CT). Contrast agents improve the definition of the spaces and organs into which they are placed by providing a physically discontinuous area within those spaces and organs.

Fluorocarbons may be introduced in a substantially pure unemulsified form into any of certain non-vascular body parts, tissues or spaces which can biologically tolerate the substance. The term "non-vascular" when used herein is intended to denote tissues and spaces which are not within the vascular system, which comprises the arterial, venous or lymphatic systems, blood and lymph vessels, vessel walls, the heart and spaces within the heart. The fluorocarbon can be introduced into the gastrointestinal tract by ingestion through the mouth in order to fill the stomach and trachea initially, and after a suitable, but typically short time, the intestine. Administration by this route allows contrast imaging of the upper gastrointestinal tract and small intestine within the abdominal area. Fluorocarbon contrast media may also be introduced by way of the rectum as an aid in imaging the lower bowel or colon.

Other body spaces which can be filled with fluorocarbon contrast media by other ports of injection so as to improve MRI, CT and conventional X-radiography imaging include volumes which could be lumens, cavities and areas such as, for example, the anterior and posterior eye spaces, the ear canals, paranasal sinuses, and the urinary bladder by way of the urethra. Also, fluorocarbon liquid can be inserted into the ureters, fallopian tubes and other parts of the genitourinary system, renal pelvises, joint spaces of the bones, lymphatic vessels and thoracic duct, the subarachnoid space, and cerebrospinal spaces including the ventricular cavities of the brain. It can also be inserted into the peritoneal cavity to enhance the imaging of structures therein. The peritoneal cavity normally and is here considered to be and includes every cavity and tissue from the diaphragm to the pelvis.

MRI images made of the abdominal contents in the absence of contrast agents and using conventional hydrogen or proton techniques will show a fairly uniform signal intensity over the area, even though the content consists of many different structures such as the fatty omentum, loops of intestine, liver, pancreas, spleen, bladder and blood vessels, because all these structures have substantial water content, therefore substantial proton content. MRI images show a bright space in areas of high proton content, because protons provide a positive signal. Effective contrast agents will have low concentration of hydrogen, and the selected body areas into which they have been inserted will appear as contrasting dark areas on MRI imaging because the signal will be absent or void in these areas.

Perfluorocarbon hydrides, like other fluorocarbons, are substantially lacking in hydrogen and rich in fluorine atoms, making them appropriate contrast agents for magnetic resonance imaging. Some fluorocarbons, such as F-44E ($C_4F_9CH-CHC_4F_9$) contain two hydrogen atoms per molecule, and perfluorocarbon hydrides contain one hydrogen atom, but even in these cases the number of hydrogen nuclei is low enough so that they are suitable as contrast agents for magnetic resonance imaging purposes. In one embodiment of the invention, the MRI system can image hydrogen in the customary manner, and the fluorocarbon compounds can be introduced neat to occupy certain body spaces, or replace water therein. Spaces filled with fluorocarbons including perfluoroctyl hydride will therefore appear as dark signal voids in a hydrogen-based MRI system image. These signal voids will distinctly contrast with the hydrogen nuclei or water concentrations in adjacent spaces or body parts.

Besides being substantially devoid of hydrogen, suitable contrast agents must have convenient physical properties which allow them to be positioned within body spaces. For example, they should be fluid or gaseous rather than solid at room temperature so that they flow easily on insertion or introduction into selected spaces. They must also be immiscible with water so that they will displace or exclude water in the space where they are positioned, and also so they will not be subject to dilution which would impair the contrasting effect. Contrast agents must also be biologically compatible, that is physiologically and chemically inert, and nontoxic.

Fluorocarbons as a class are hydrophobic or immiscible in water. They will thus exclude or displace water from the body space where they are placed and will not become diluted by aqueous body fluids. Perfluoroctyl hydride, as a non-brominated fluorocarbon, is somewhat more lipophobic than contrast agents such as perfluoroctyl bromide (PFOB) and perfluorohexyl bromide (PFHB). The trivial absorption of PFOB from the lumen of the gut is exceeded by that of PFHB. PFOH is less likely than either to be absorbed into the tissues of the body, hence more readily excreted and less of a potential toxic hazard.

The suitability of perfluorooctyl hydride, (PFOH) and other perfluorocarbon hydrides for use in the present invention is surprising. Among similar organic hydrides, the C—H group has a reactive acidic C—H proton. Prior to the present invention, it was believed on the basis of analogy to close chemical analogues that perfluorohydrides were acidic and therefore chemically reactive. This assumption is not verified by laboratory investigation. If PFOH were a reactive hydride, the following reaction should occur when it is treated with a base:

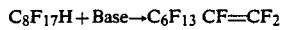

$$C_8F_{17}H + Base \rightarrow C_6F_{13}\,CF = CF_2$$

Such reactive compounds would be toxic and unsuitable for physiological use. However, when PFOH was treated with a series of strong bases, only the strongest of the series, $C_4HgLi$, brought about the predicted reaction (Example 2).

Experimental animal studies indicate that, consistent with its demonstrated lack of chemical reactivity, PFOH is well tolerated in vivo, having a low toxicity that is comparable to other fluorocarbons such as perfluoroctyl bromide (PFOB). Chronic toxicity studies of PFOH and PFOH-containing fluorochemicals, Examples 3 and 4, were performed with neat or pure fluorocarbons injected intraperitoneally and also with emulsions of fluorochemicals injected intravenously. Intraperitoneal studies are a proven technique for producing prolonged tissue exposure to fluorochemicals, since the fluorochemicals are eliminated from the peritoneal cavity at a slower rate than that following any other mode of injection, and also because it is possible to administer massive doses of fluorochemicals into the peritoneal cavity. We have administered as much as 100 ml/kg (193 g/kg) intraperitoneally in mice. It is difficult to administer more than 40 g/kg of fluorochemical emulsions intravenously due to volume overload and congestive failure. Example 5 lists the series of chronic intraperitoneal studies performed with PFOB as composition L-1913 (substantially pure) and L-6984 (PFOB with 1.4% PFOH, also designated FC 3876). Comparative information is given on the intraperitoneal tolerance of perfluoroctylhydride (PFOH), perfluorohexylbromide (PFHB), perfluorodecalin (PFDC) and perfluorotributylamine (PFTB). All of the mice that received PFOH continue to survive and appear healthy more than 11 months after dosing with 20 ml/kg and 9 months after dosing with 100 ml/kg.

Chronic toxicity studies were also carried out on the tolerance of PFOH emulsions given intravenously (Example 6). Emulsions containing 20% PFOH were prepared according to the procedure disclosed in U.S. patent application Ser. No. 140,543, filed Jan. 4, 1988. This disclosure is herein incorporated by reference. All of the members of the groups given doses of 10 g/kg and 5 g/kg survived at least 3 months.

Perfluoroctyl hydride is more volatile than the corresponding brominated fluorocarbon PFOB as indicated by physical measurements. The boiling point of PFOH is 109°–110° C.; that of PFOB is 140°–141° C. Also, retention time on gas chromatography is less: 2.1 min for PFOH, 2.8 min for PFOB. It is less volatile than the next lower analogue PFHB which boils at 98° C.. The vapor pressure of PFOH, 24 mmHg, is intermediate between that of PFOB at 14 mm Hg, and PFHB at 90 mm Hg. (Boiling points determined at 760 mm; vapor pressures at 37° C.).

Because of its volatility, PFOH vaporizes rapidly at body temperature. Vaporization of a contrast agent is not dangerous if it occurs in a non-vascular space; and in some contrast agent sites, rapid vaporization at body temperatures is highly advantageous. Vapor phase occupies much more space than the corresponding amount of material in the liquid phase and so a smaller volume, less expensive dose is required. PFOH is particularly useful when the contrast agent is used as a bowel marker not only because if its volatility, but also because of its lipophobicity, which reduces the likelihood that it will be absorbed from the gastrointestinal tract before it is excreted. The selection of an oral contrast agent should be based on its volatility, its absorption in the gut, and its cost. The ideal agent has high vapor pressure, low absorption and minimal cost. PFOH has a vapor pressure intermediate between the two fluorocarbon bromides, PFOB and PFHB; however, since PFOH is less readily absorbed than either, it is the preferred agent when this criterion is weighted.

Both the gas phase and liquid phase of PFOH are excellent bowel markers both on X-ray and MRI. Fluorocarbon gas, as well as the liquid, appears black on the $T_1$ and $T_2$ weighted images of MRI. The gas phase as well as the liquid also appear black on CT.

Use of perfluorocarbon mixtures containing perfluorocarbon hydrides in combination with perfluorocarbon bromides is both convenient and economical. PFOH can be advantageously used in combination with the perfluorocarbon bromides in several imaging application. Brominated perfluorocarbons are an essential component of perfluorocarbon mixtures used in radiographic procedures requiring high radiodensity. However, where the bromides alone are so dense as to produce artifacts on computed tomography images, PFOH can act as a diluent to proportionally reduce the radiodensity. These mixtures of PFOH and PFOB are particularly useful as an oral contrast agents for CT. Imaging composition for intravascular use having small concentrations of perfluorocarbon hydrides are less costly to produce than pure fluorocarbon bromide composition and are equally safe and effective.

PFOH is found in varying concentrations as a contaminant in preparations of PFOB. It becomes increasingly expensive to reduce PFOH to increasingly low levels in these preparations. A PFOB preparation virtually free of PFOH, designated L-1913, is twice as expensive to prepare as a preparation designated L 6984 containing 1.4% PFOH.

We have found that (based on studies of chemical reactivity, and acute, subacute and chronic toxicity in animals), the presence of small amounts of PFOH in PFOB preparations used intravascularly is innocuous and that preparations such as L-1913 and L-6984 are pharmaceutically equivalent when used for this purpose.

Imaging compositions used intravascularly for magnetic resonance imaging which comprise PFOH together with PFOB perform as well as those comprising PFOB alone, as indicated by studies on the distribution of fluorocarbons in the tissues of experimental animals with implants of colon and mammary tumors (Examples 5 & 6). Although there appear to be some differences in the distribution between L-1913 and L-6984, those differences are not consistent, and provide no evidence that the presence of PFOH lowers the tissue levels of PFOB. In all cases the quantities of PFOB in the tissues were adequate for imaging studies. These data, together with that on in vivo toxicity (Examples 3 and 4) and the imaging studies described in Example 1 indicate substantially identical performance for L-1913 and L-6984. Further, the evidence that imaging compositions comprising low concentration of PFOH are well tolerated indicates that the tendency of PFOH to vaporize at body temperatures is not a contraindication to its intravascular use at this level of concentration.

The use of PFOB emulsions for the transport of oxygen to the tissues of the body is known. Emulsions such as L-6984 comprising low concentrations of PFOH, are functionally equivalent to substantially pure PFOB emulsions and can be used similarly. PFOB/PFOH emulsions can be loaded with oxygen in a manner identical to that used for preparing the corresponding PFOB-$O_2$ emulsions. Oxygen is highly soluble in the perfluorocarbons and in particular those that are monobrominated. Emulsified imaging compositions comprising small amounts of PFOH in combination with a perfluorocarbon bromide are prepared as described previously, by passage of the fluorocarbons, emulsifying agents and other components in an aqueous media through a high pressure fluidizing apparatus generating high shear forces. Oxygen is next dissolved in the prepared emulsion according to the procedure disclosed in U.S. patent application Ser. No. 140,543, filed Jan. 4, 1988. This disclosure is herein incorporated by reference.

Many other objects, features, and advantages of the present invention will be apparent to those skilled in the art.

Although the invention has been described in the context of certain preferred embodiments, it will be understood that the invention is intended only to be limited by the lawful scope of the claims that follow and equivalence thereof.

EXAMPLE 1

Magnetic Resonance Imaging of the Gastrointestinal Tract Using Perfluorocarbons as Contrast Agents Four rats were given oral doses of perfluoroctyl bromide (PFOB), perfluorohexyl bromide (PFHB), a perfluoroctyl hydride (H) and a perfluorocarbon ether, $C_4F_9CH$—$CHC_4F_9$ (E). Each rat received one of these four compounds at a dose of 16 ml/kg. Thirty minutes later, the rates were sacrificed by cervical dislocation. They were placed prone in the magnet utilizing a 20 cm cylindrical coil. Along with the rats, each of the fluorocarbons was mixed with equal volume of tap water and placed in a 2 cm cylinder to be scanned. A tap water-filled syringe was also placed near the PFOB mixture for orientation and identification. Rats were scanned first in the coronal plane in a 5 mm scan thickness with TR 800 TE 20 (hydrogen density) and TE 70 ($T_2$ weighted). The latter series was obtained in 3 mm scan thicknesses obtained every 4.5 mm.

Findings:

All rats demonstrated significant darkening of bowel with very little fluorocarbon still present in the stomach. On these images, there was no significant difference in the degree of darkening of bowel between the various compounds. The degree of filling was almost complete except for stomach and colon, however, the colon was air-filled and is difficult to differentiate from PFOB.

When evaluating the fluorocarbon water mixture, there was no mixing between the water and the fluorocarbon in any of the compartments. There was no signal observed for PFOB or PFHB. These images were not labeled as to which of the other two fluorocarbons were H and E, however, both of these fluorocarbons had a faint signal with one almost twice as bright as the other on the hydrogen density weighted images. Interestingly on the $T_2$ weighted images, the signal observed from these two fluorocarbons reversed in that the one that was brighter became darker and the one that was darker became brighter suggesting that the material with more hydrogens in it had a shorter $T_2$ for its hydrogen than the material that had less hydrogen in it. However, the images of the rats do not show a significant difference between any of the fluorocarbons. Perhaps the PFC with less hydrogen and longer $T_2$ is slightly brighter than the rest on $T_2$ weighted images, but still reasonably dark.

EXAMPLE 2

Chemical Reactivity of Perfluoroctylhydride (PFOH)

EXAMPLE 2

CHEMICAL REACTIVITY OF PERFLUOROCTYLHYDRIDE (PFOH)

| Basic Reactant | Reaction Conditions | Results |
| --- | --- | --- |
| $CaH_2$ | 1,4-dioxane reflux 12 days at 100° C. | No reaction |
| $CaH_2$ | Triglyme (1,2-bis [2 methoxyethoxy] ethane 12 days at 160° C. | No reaction |
| NaH | Triglyme 19 hr at 160° C. | No reaction |
| NaH | 1,4-dioxane reflux 42 hr at 100° C. | No reaction |
| $NaAlH_2$ $(OCH_2CH_2OCH_3)_2$ | Benzene reflux 42hr at 80° C. | No reaction |
| $C_6F_{13}$ + H + $Br_2$ | Sealed tube, reflux overnight with 500 watt photo lamp | No reaction |
| Using the strongest base available, the following reaction occurred: | | |
| $C_8F_{17}$-H + n $C_4H_9Li$ | → [0° C., Hexane, 1–2 min reaction time] | $C_6F_{13}CF$ = $CF_2$ (70% yield) |

EXAMPLE 3

Perfluorochemical Toxicity Studies Intraperitoneal Injection

EXAMPLE 3

PERFLUOROCHEMICAL TOXICITY STUDIES INTRAPERITONEAL INJECTION

| Date | No. of Mice | Compound | Dose (ml/kg) | Results |
| --- | --- | --- | --- | --- |
| (1983) | | | | |
| 1–19 | 10 | PFOB (L-1913) | 40 | All survived longer than three months without signs of toxicity. |
| 1–19 | 10 | PFHB ($C_6F_{13}Br$) | 40 | All survived longer than three months without signs of toxicity. |
| 1–19 | 4 | PFDC (Perfluorodeclin) | 40 | Sacrificed 1 month later without signs of toxicity. |
| 1–19 | 4 | PFTB (Perfluorotributylamine) | 40 | Sacrificed 1 month later without signs of toxicity. |
| 4–13 | 3 | PFOB + 1.4% PFOB (L-6984) | 40 | One died 6-84, one died 7-1-84 and one sacrificed 7-5-84 |
| 8–19 | 5 | PFOH | 20 | All continue to survive without signs of toxicity. |
| 10–17 | 10 | PFOH | 100 | All continue to survive without signs of toxicity. |
| 11–07 | 4 | PFOB (L-1913) | 100 | One mouse sacrificed 6-28-84. Three mice survive without signs |

EXAMPLE 3-continued

PERFLUOROCHEMICAL TOXICITY STUDIES
INTRAPERITONEAL INJECTION

| Date | No. of Mice | Compound | Dose (ml/kg) | Results |
|---|---|---|---|---|
| (1984) | | | | of toxicity. |
| 3–05 | 10 | PFOB + 1.4% PFOH (L-6984) | 100 | All continue to survive without signs of toxicity |

EXAMPLE 4

Perfluoroctylhydride (PFOH) Emulsion Toxicity Studies-Intravenous

EXAMPLE 4

PERFLUOROCTYLHYDRIDE (PFOH) EMULSION
TOXICITY STUDIES-INTRAVENOUS

| Date | No. Mice | Emulsion | Dose* (g/kg) | Results |
|---|---|---|---|---|
| (1983) | | | | |
| 11–16 | 5 | 20% PFOH 4% Lecithin | 10 | 1 died 4 days after injection, 4 sacrificed 2 weeks after injection without signs of toxicity. |
| (1984) | | | | |
| 4–26 | 10 | 20% FOH 5% Lecithin | 10 | The hair of mice was scruffy for 4 days after which the appearance and behavior was normal. |
| 4–26 | 10 | 20% FOH 5% Lecithin | 5 | All continue to survive without signs of min. toxicity. |

*All doses administered at the rate of 1.1 ml/min.

EXAMPLE 5

Effects of PFOH in PFOB Emulsion on Tissue Fluorocarbon Levels

EXAMPLE 5

Effects of PFOH in PFOB Emulsion on Tissue Fluorocarbon Levels

| PFOH/PFOB Ratio | No. Mice | Fluorocarbon Concentration in situ (mg/gm tissue) | | |
|---|---|---|---|---|
| | | Tumor | Liver | Spleen |
| 0% | 6 | 2.91 ± .23 | 6.58 ± .51 | 3.76 ± .30 |
| 2% | 5 | 2.44 ± .40 | 9.13 ± 1.84 | 6.74 ± 1.07 |
| 10% | 7 | 2.47 ± .32 | 6.44 ± .45 | 4.93 ± .48 |

Mice with implants of Colon Tumor 26 (CT-26) received PFOB emulsion or an emulsion of PFOB+PFOH in a dose of 10 g/kg and were sacrificed 48 hours later.

EXAMPLE 6

Comparative Effectiveness of L-1913 and L-6984 as Tumor Imaging Agents

EXAMPLE 6

Comparative Effectiveness of L-1913 and L-6984 as Tumor Imaging Agents

| Tumor | Emulsion | No. Mice | Fluorocarbon Concentration in situ (mg/gm tissue) | | |
|---|---|---|---|---|---|
| | | | Tumor | Liver | Spleen |
| EMT-6 Exp #1 | L-1913 | 9 | 1.78 ± .12 | 8.74 ± .55 | 3.91 ± .29 |
| | L-6984 | 8 | *2.48 ± .17 | 8.16 ± .57 | *2.59 ± .26 |
| EMT-6 Exp #2 | L-1913 | 7 | 1.66 ± .32 | | 4.48 ± .21 |
| | L-6984 | 8 | 1.44 ± .10 | | 5.25 ± .45 |
| CT-26 | L-1913 | 10 | *2.21 ± .24 | | |
| | L-6984 | 10 | 1.24 ± .11 | | |

*p < .01

All mice received 10 g/kg PFOB 20% w/v emulsion with lecithin as emulsifier, and were sacrificed 48 hours later. EMT-6 refers to Experimental Mammary Tumor 6 and CT-26 signifies Colon Tumor 26, the two types of experimental tumors used in this study.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced with their scope.

What is claimed and desired to be secured by United States Letters Patent is:

1. A fluorocarbon emulsion for use in an animal body, comprising:
   a physiologically acceptable aqueous phase;
   a perfluorocarbon mixture, comprising a perfluorocarbon bromide having from 6 to 10 carbon atoms, and at least 0.1% of a perfluorocarbon hydride having from 6 to 10 carbon atoms, at a total concentration of 20% to 125% weight per volume in said emulsion; and
   an effective amount of an emulsifying agent.

2. The emulsion of claim 1 comprising an effective oxygen-carrying amount of said perfluorocarbon mixture.

3. The emulsion of claim 1 or 2 wherein said perfluorocarbon bromide is perfluoroctyl bromide.

4. The emulsion of claim 1 or 2 wherein said perfluorocarbon hydride is perfluoroctyl hydride.

5. The emulsion of claim 1 or 2 wherein said emulsifying agent is a phospholipid.

6. A method for imaging a selected tissue of an animal body, comprising introducing the emulsion of claim 1 or 2 into the vascular system of said body.

7. A method for carrying oxygen to the tissues of an animal body, comprising the introduction of the emulsion of claim 2 into the vascualr system of said body.

* * * * *